US010301553B2

(12) United States Patent
Geissler et al.

(10) Patent No.: US 10,301,553 B2
(45) Date of Patent: May 28, 2019

(54) USE OF SULFONIUM SALTS AS HYDROGEN SULFIDE INHIBITORS

(71) Applicant: Ecolab USA Inc., St. Paul, MN (US)

(72) Inventors: Brett Geissler, Richmond, TX (US); Ashish Dhawan, Naperville, IL (US)

(73) Assignee: Ecolab USA Inc., St. Paul, MN (US)

( * ) Notice: Subject to any disclaimer, the term of this patent is extended or adjusted under 35 U.S.C. 154(b) by 0 days.

(21) Appl. No.: 15/445,707

(22) Filed: Feb. 28, 2017

(65) Prior Publication Data

US 2018/0245004 A1    Aug. 30, 2018

(51) Int. Cl.
| C10L 1/24 | (2006.01) |
| C10G 29/28 | (2006.01) |
| A01N 31/08 | (2006.01) |
| C02F 1/68 | (2006.01) |
| C09K 8/532 | (2006.01) |
| C02F 101/10 | (2006.01) |

(52) U.S. Cl.
CPC ............ *C10G 29/28* (2013.01); *A01N 31/08* (2013.01); *C02F 1/68* (2013.01); *C09K 8/532* (2013.01); *C02F 2101/101* (2013.01); *C09K 2208/20* (2013.01); *C09K 2208/32* (2013.01)

(58) Field of Classification Search
CPC ............................... C10G 29/28; A01N 31/08
USPC .............................................................. 585/2
See application file for complete search history.

(56) References Cited

U.S. PATENT DOCUMENTS

| 464,330 | A |   | 4/1937 | Groves |
| 2,596,450 | A |   | 5/1952 | Wachter et al. |
| 2,807,648 | A |   | 9/1957 | Pitt |
| 2,941,949 | A |   | 6/1960 | Saukaitis |
| 2,947,691 | A | * | 8/1960 | Bennett .................. C09K 8/605 507/245 |
| 3,277,008 | A |   | 10/1966 | Heit |
| 3,300,375 | A |   | 1/1967 | Wehner |
| 3,538,229 | A |   | 11/1970 | Ratts |
| 3,668,137 | A |   | 6/1972 | Gardner |
| 4,180,469 | A |   | 12/1979 | Anderson |
| 4,374,066 | A |   | 2/1983 | Crivello et al. |
| 4,400,541 | A |   | 8/1983 | Iyer |
| 4,451,409 | A |   | 5/1984 | Buske et al. |
| 4,659,594 | A |   | 4/1987 | Wu |
| 4,864,075 | A | * | 9/1989 | Thompson ............ B01D 17/047 210/705 |
| 5,320,805 | A |   | 6/1994 | Kramer et al. |
| 5,397,398 | A |   | 3/1995 | Van Vlahakis et al. |
| 6,214,777 | B1 | * | 4/2001 | Li ......................... A01N 29/04 428/35.7 |
| 6,756,013 | B1 |   | 6/2004 | Cornell et al. |
| 7,493,955 | B2 |   | 2/2009 | Gupta et al. |
| 8,177,963 | B2 |   | 5/2012 | Greaney et al. |
| 8,821,805 | B2 |   | 9/2014 | Luo et al. |
| 9,127,239 | B2 |   | 9/2015 | Garner |
| 9,279,086 | B2 |   | 3/2016 | Hardacre et al. |
| 2004/0179066 | A1 |   | 9/2004 | Arita et al. |
| 2005/0148679 | A1 |   | 7/2005 | Chiu et al. |
| 2010/0022801 | A1 |   | 1/2010 | Shinya |
| 2010/0256019 | A1 |   | 10/2010 | Aston et al. |
| 2011/0031165 | A1 |   | 2/2011 | Karas et al. |
| 2011/0118165 | A1 |   | 5/2011 | Lee |
| 2011/0192639 | A1 |   | 8/2011 | Shinya et al. |
| 2011/0282114 | A1 |   | 11/2011 | Luo et al. |
| 2012/0034313 | A1 |   | 2/2012 | Wrangham et al. |
| 2013/0004378 | A1 |   | 1/2013 | Luo et al. |
| 2013/0154129 | A1 |   | 6/2013 | Sul et al. |
| 2014/0371495 | A1 |   | 12/2014 | Anderson et al. |
| 2015/0080271 | A1 |   | 3/2015 | DeWolf et al. |
| 2015/0107832 | A1 |   | 4/2015 | DeWolf et al. |
| 2015/0191659 | A1 |   | 7/2015 | Anderson et al. |
| 2016/0032177 | A1 |   | 2/2016 | Howe et al. |
| 2016/0137904 | A1 |   | 5/2016 | Drake et al. |
| 2016/0222762 | A1 |   | 8/2016 | Geissler et al. |
| 2017/0329227 | A1 |   | 11/2017 | Ohashi et al. |

FOREIGN PATENT DOCUMENTS

| DE | 19610745 A1 | 9/1997 |
| EP | 0 013 462 A1 | 7/1980 |
| FR | 2467547 A1 | 4/1981 |
| FR | 2476078 A1 | 8/1981 |
| GB | 2294902 A | 5/1996 |

(Continued)

OTHER PUBLICATIONS

Murakami (Machine Translation of JP2013-185017). (Year: 2013).*
Jellali, et. al. "Antifouling activity of novel polyisoprene-based coatings made from photocurable natural rubber derived oligomers", Progress in Organic Coatings, 76 (2013); pp. 1203-1214. (Year: 2013).*
Hirayama (Machine Translation of JP2006-232800) (Year: 2006).*
SciFinder, Notes from PCT International Application 2002048101, Jun. 20, 2002, 3 pages.
Akhtar, S.R. et al., Synthesis of Aryl-Substituted Sulfonium Salts by the P205-Methanesulfonic Acid Promoted Condensation of Sulfoxides with Aromatic Compounds, J. Org. Chem. 1990, 55, pp. 4222-4225.
Shiraishi, Yasuhiro et al., A Novel Desulfurization Process for Fuel Oils Based on the Formation and Subsequent Precipitation of S-Alkylsulfonium Salts. 2. Catalytic-Cracked Gasoline, Ind. Eng. Chem. Res. 2001, 40, pp. 1225-1233.

(Continued)

*Primary Examiner* — Philip Y Louie
*Assistant Examiner* — Aaron W Pierpont
(74) *Attorney, Agent, or Firm* — Stinson Leonard Street LLP

(57) ABSTRACT

Uses of aryl sulfonium salts for lowering sulfide concentrations and for preventing growth of microbes in a water injection system, a hydrocarbon extraction system, or a hydrocarbon production system are disclosed. Treating oilfield injection and produced fluids containing high levels of microbes with aryl sulfonium salts can significantly decrease the amount of hydrogen sulfide produced, which can be used to measure sulfidogenesis. The treatment can also decrease the number of active microbes in the injection and produced fluids. Thus, these aryl sulfonium salts can be effectively used as inhibitors of hydrogen sulfide generation and as biocides in oilfield fluids.

13 Claims, No Drawings

(56) References Cited

FOREIGN PATENT DOCUMENTS

| | | |
|---|---|---|
| JP | 2008044881 A | 2/2008 |
| WO | 01/23504 A1 | 4/2001 |
| WO | 2007/101397 A1 | 9/2007 |
| WO | 2008/016662 A2 | 2/2008 |
| WO | 2011/037773 A2 | 3/2011 |
| WO | 2012/120278 A1 | 9/2012 |
| WO | 2014/165813 A1 | 10/2014 |

OTHER PUBLICATIONS

Shiraishi, Yasuhiro et al., A Novel Desulfurization Process for Fuel Oils Based on the Formation and Subsequent Precipitation of S-Alkylsulfonium Salts. 1. Light Oil Feedstocks, Ind. Eng. Chem. Res. 2001, 40, pp. 1213-1224.

Sun, Wenjie et al., Biodegradability, Cytotoxicity, and Physicochemical Treatability of Two Novel Perfluorooctane Sulfonate-Free Photoacid Generators, Arch Environ Contam Toxicol (2013) 64 pp. 187-197.

"Bacteria in the Oil Field" Currents in Research and Technology, The Technical Review, vol. 37, No. 1, pp. 48-53 (1989).

Crowe, Curtis W. et al., Acid Corrosion Inhibitor Adsorption and its Effect on Matrix Stimulation Results, Society of Petroleum Engineers AIME (SPE 10650) (1982), pp. 59-65.

Atta, Ayman M. et al., A New Green Ionic Liquid-Based Corrosion Inhibitor for Steel in Acidic Environments, Molecules 2015, 20, pp. 11131-11153.

Frenier, Wayne W. et al., A Mechanistic Study of Sulfonium Salts Acting as Ferric Ion Corrosion Inhibitors, Corrosion-NACE, vol. 36, No. 7, Jul. 1980, pp. 323-327.

Horner, Von L.. et al., Identification of the secondary inhibitors of some sulfoxides, triphenyl arsene oxide, and some sulfonium salts, Werkstoffe Und Korrosion, vol. 22, No. 11, pp. 930-933 (Nov. 1971).

Ledovskikh, V.M., Influence of Spatial Structure on the Inhibiting Properties of Monofunctional and Polyfunctional Organic Substances, English translation of Zaschita Metallov, vol. 18, No. 4, pp. 494-497 (Jul.-Aug. 1982).

Martinez-Palou, Rafael et al., Perspectives of Ionic Liquids Applications for Clean Oilfield Technologies, Ionic Liquids: Theory, Properties, New Approaches, www.intechopen.com, (Feb. 2011), pp. 567-630.

Rostami, A. et al., Review and Evaluation of Corrosion Inhibitors Used in Well Stimulation, Society of Petroleum Engineers 121726 (2009), pp. 1-17.

The Technical Review, PVT Analysis for Oil Reservoirs, Reservoir of Engineering, vol. 37, No. 1 (Jan. 1989), 53 pages.

Scendo, M. et al., The Effect of Ionic Liquids on the Corrosion Inhibition of Copper in Acidic Chloride Solutions, International Journal of Corrosion, vol. 2011, Article ID 718626 (2010), 14 pages.

Scendo, M. et al., Inhibition Effect of 1-Butyl-4-Methylpyridinium Tetrafluoroborate on the Corrosion of Copper in Phosphate Solutions, International Journal of Corrosion, vol. 2011, Article ID 761418 (2011), 13 pages.

Uehara, Jun et al., A Surface-Enhanced Raman Spectroscopy Study on Adsorption of Some Sulfur-Containing Corrosion Inhibitors on Iron in Hydrochloric Acid Solutions, J. Electrochem. Soc., vol. 138, No. 11, Nov. 1991, pp. 3245-3251.

\* cited by examiner

USE OF SULFONIUM SALTS AS HYDROGEN SULFIDE INHIBITORS

FIELD OF THE INVENTION

The present invention generally relates to the use of aryl sulfonium salts for inhibiting hydrogen sulfide production by a microorganism in a hydrocarbon-containing system comprising a water injection system, a hydrocarbon extraction system, or a hydrocarbon production system.

BACKGROUND OF THE INVENTION

The introduction of sulfate- and sulfur-containing waters into oil fields for secondary oil recovery often leads to formation of undesirable sulfur-containing compounds, particularly hydrogen sulfide, by sulfur-utilizing prokaryotes. These sulfur-containing compounds lead to safety, environmental, corrosion and plugging problems, and even premature abandonment of the oil and gas field.

Particularly, hydrogen sulfide generation begins by introducing sulfate- or other sulfur-containing aqueous solutions such as seawater into an anaerobic environment for indigenous microorganisms and microorganisms contained in the introduced aqueous solutions that are capable of producing hydrogen sulfide.

Hydrogen sulfide is a toxic, corrosive, flammable gas that causes problems in both the upstream and downstream oil and gas industry. Exposure to this gas, even at low concentrations, can cause serious injury or death. Hydrogen sulfide ($H_2S$) in natural gas and crude oil reserves is often accompanied by small amounts of mercaptans (RSH), sulfides ($R_2S$), polysulfides, and carbonyl sulfide (COS). Considerable expense and effort are expended annually to reduce the $H_2S$ content of gas and oil streams to make them suitable for commercial use.

Hydrogen sulfide has an offensive odor, and natural gas and crude oil streams containing substantial amounts of $H_2S$ are considered "sour." In addition to natural gas and petroleum, there are also aqueous fluids that must be treated to reduce or remove $H_2S$, such as waste water streams. Treatments to reduce or remove $H_2S$ from hydrocarbon or aqueous streams are referred to as "sweetening" treatments because the odor of the processed products is improved by the absence of hydrogen sulfide.

In some cases, nitrate introduction has been used to prevent sulfide formation in waters because specific nitrate-reducing bacteria (NRB) are activated and use volatile fatty acids (VFAs) and the carbon dioxide from dissolved limestone in the formation to produce nitrogen and/or ammonia. Thus, the NRBs could compete with the sulfur-utilizing prokaryotes and more rapidly use the VFAs, resulting in lowered production of sulfide and sulfur-containing compounds by the sulfur-utilizing prokaryotes.

However, this nitrate treatment can cause problems if the treatment is suspended or stopped because the hydrogen sulfide production would resume at the previous concentrations or the hydrogen sulfide production could even increase due to the enhanced biomass present. Additionally, some instances of nitrate application to reduce hydrogen sulfide have increased corrosion due to the incomplete reduction of the applied nitrate. The increased amount of NRBs can also lead to injectivity issues, where the microbial population blocks the injection path of the water into the reservoir.

Thus, a need exists for an effective and efficient method to prevent the generation of hydrogen sulfide and reduce the growth of or kill the microbes responsible for the production of hydrogen sulfide in a hydrocarbon-containing system comprising a water injection system, a hydrocarbon extraction system, or a hydrocarbon production system.

SUMMARY OF THE INVENTION

One aspect of the invention is reducing or preventing the reduction of a sulfur-containing compound and production of hydrogen sulfide by a microorganism in a hydrocarbon-containing system comprising a water injection system, a hydrocarbon extraction system, or a hydrocarbon production system. The method comprises administering an effective amount of an aryl sulfonium salt into the water injection system, the hydrocarbon extraction system, or the hydrocarbon production system.

Another aspect is a method for reducing a concentration of hydrogen sulfide in a hydrocarbon-containing system comprising a water injection system, a hydrocarbon extraction system, or a hydrocarbon production system comprising administering an effective amount of an aryl sulfonium salt into the water injection system, the hydrocarbon extraction system, or the hydrocarbon production system, wherein the aryl sulfonium salt inhibits the production of hydrogen sulfide by a sulfur utilizing prokaryote.

Other objects and features will be in part apparent and in part pointed out hereinafter.

DESCRIPTION OF THE PREFERRED EMBODIMENTS

The present invention is directed to methods for reducing or preventing the reduction reaction of a sulfur-containing compound by a microorganism that produces hydrogen sulfide in a hydrocarbon-containing system comprising a water injection system, a hydrocarbon extraction system, or a hydrocarbon production system comprising administering an effective amount of an aryl sulfonium salt into the water injection system, the hydrocarbon extraction system, or the hydrocarbon production system. Oilfield produced fluids or seawater, where each contains high levels of microorganisms, can be treated with aryl sulfonium salts that can significantly decrease the amount of microorganisms and their activity in the fluids. In particular, the microorganisms can be involved in the reduction reaction of sulfur-containing compounds that produce hydrogen sulfide. The treatment with the aryl sulfonium salts can also significantly decrease the amount of hydrogen sulfide produced. Thus, these aryl sulfonium salts can be effectively used as sulfidogenesis inhibitors and biocides in oilfield fluids.

One aspect of the invention is a method for reducing or preventing growth of a microorganism in a hydrocarbon-containing system comprising a water injection system, a hydrocarbon extraction system, or a hydrocarbon production system comprising administering an effective amount of a substituted or unsubstituted aryl sulfonium salt into the water injection system, the hydrocarbon extraction system, or the hydrocarbon production system.

Another aspect of the invention is a method for lowering sulfide concentration in a hydrocarbon-containing system comprising a water injection system, a hydrocarbon extraction system, or a hydrocarbon production system comprising administering an effective amount of an aryl sulfonium salt into the water injection system, the hydrocarbon extraction system, or the hydrocarbon production system, wherein the aryl sulfonium salt inhibits the production of sulfide by a sulfide utilizing prokaryote.

In the methods described herein, the aryl sulfonium salt can comprise a cation or a dication of Formulae 1, 2, or 3:

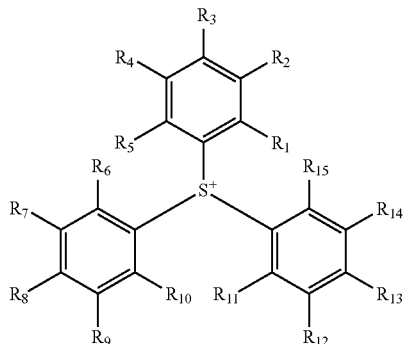

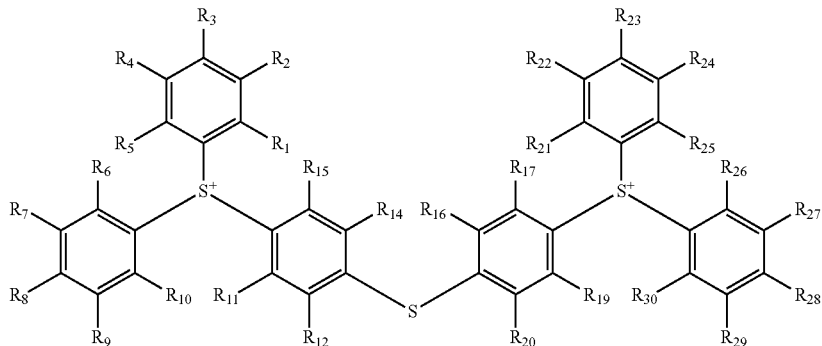

wherein $R_1$-$R_{30}$ are independently hydrogen, alkyl, alkoxy, aryl, or heterocyclo.

For the methods described herein, the aryl sulfonium salt can comprise a cation or a dication of Formula 1.

Additionally, the aryl sulfonium salt can comprise a cation or a dication of Formula 2.

Further, the aryl sulfonium salt can comprise a cation or a dication of Formula 3.

Also, the aryl sulfonium salt can comprise a cation or a dication of Formulae 1 and 2.

For the methods herein, the aryl sulfonium salt can comprise a cation or a dication of Formulae 1 and 3.

Also, the aryl sulfonium salt can comprise a cation or a dication of Formulae 2 and 3.

Additionally, the aryl sulfonium salt can comprise a cation or a dication of Formulae 1, 2, and 3.

For the aryl sulfonium salts of 1, 2, and 3, one to six of $R_1$-$R_{30}$ can independently be alkyl and the balance can be hydrogen; further, one to three of $R_1$-$R_{30}$ can independently be alkyl and the balance can be hydrogen; preferably, $R_1$-$R_{30}$ are hydrogen.

The aryl sulfonium salt can be administered by injecting an injection fluid into the hydrocarbon extraction system or the hydrocarbon production system.

For the methods described herein, the water injection system, the hydrocarbon extraction system, or the hydrocarbon production system can be a subterranean hydrocarbon-containing formation, a well, a pipeline, a fluid separation vessel, a floating production storage vessel, an offloading vessel, a refinery, or a storage system.

Further, the hydrocarbon extraction or the hydrocarbon production system can be a subterranean hydrocarbon-containing formation.

In the methods described herein, the aryl sulfonium salt can further be administered with a biocide, administered with a calcium nitrate/perchlorate agent, administered with a preservative agent, combined with a method for removing sulfate, administered with a scale inhibitor, administered with an $H_2S$ scavenger, or a combination thereof.

The sulfonium salt can be administered by injecting an injection fluid into the hydrocarbon extraction system or the hydrocarbon production system. The injection fluid can comprise sea water, produced water, fresh water, brackish water, drilling fluid, completion fluid, or a combination thereof.

The microorganism can comprise a sulfur utilizing prokaryote. The sulfur utilizing prokaryote can produce hydrogen sulfide through the reduction of sulfate, thiosulfate, sulfite, bisulfite, sulfur, other inorganosulfur compounds, organosulfur compounds, or a combination thereof.

For the methods described herein, the aryl sulfonium salt can be injected into the water injection system, the hydrocarbon extraction system, or the hydrocarbon production system continuously with the injection fluid.

Further, the aryl sulfonium salt can be injected into the water injection system, the hydrocarbon extraction system, or the hydrocarbon production system intermittently with the injection fluid. When the aryl sulfonium salt is injected into the hydrocarbon extraction or production system intermittently, the injection of the aryl sulfonium salt can occur every one to four hours, one to four days, or one to four weeks.

The sulfur utilizing prokaryote can comprise a genus or species of bacteria and archaea capable of reducing sulfur compounds to produce sulfide.

Preferably, the sulfur utilizing prokaryote can comprise a sulfate-reducing bacteria.

For the methods described herein, the aryl sulfonium salt can be triarylsulfonium chloride, triarylsulfonium nitrate, triarylsulfonium bromide, triarylsulfonium iodide, triarylsulfonium hexafluorophosphate, triarylsulfonium perchlorate, triarylsulfonium hexafluoroarsenate, triarylsulfonium p-toluenesulfonate, triarylsulfonium acetate, triarylsulfonium phosphate, diaryl (4-phenylthio)arylsulfonium chloride, diaryl (4-phenylthio)arylsulfonium nitrate, diaryl (4-phenylthio)arylsulfonium bromide, diaryl (4-phenylthio) arylsulfonium iodide, diaryl (4-phenylthio)arylsulfonium hexafluorophosphate, diaryl (4-phenylthio)arylsulfonium perchlorate, diary (4-phenylthio)arylsulfonium hexafluoroarsenate, diaryl (4-phenylthio)arylsulfonium p-toluenesulfonate, diaryl (4-phenylthio)arylsulfonium acetate, diaryl (4-phenylthio)arylsulfonium phosphate, (thiodi-4,1-phenylene)bis-diarylsulfonium dichloride, (thiodi-4,1-phenylene)bis-diarylsulfonium dinitrate (thiodi-4,1-phenylene) bis-diarylsulfonium dibromide, (thiodi-4,1-phenylene)bis-diarylsulfonium diiodide, (thiodi-4,1-phenylene)bis-diarylsufonium dihexafluorophosphate, (thiodi-4,1-phenylene)bis-diarylsulfonium dipechlorate (thiodi-4,1-phenylene)bis-diarylsulfonium dihexafluoroarsenate, diaryl (thiodi-4,1-phenylene)bis-diarylsulfonium di-p-toluenesulfonate, (thiodi-4,1-phenylene)bis-diarylsulfonium diacetate, (thiodi-4,1-phenylene)bis-diarylsulfonium diphosphate, or a combination thereof. More preferably, the aryl sulfonium salt can comprise triphenyl sulfonium chloride or alternatively, the aryl sulfonium salt can comprise diphenyl (4-phenylthio)phenylsulfonium chloride or the aryl sulfonium salt can comprise (thiodi-4,1-phenylene)bis-diphenylsulfonium dichloride.

The aryl sulfonium salts are commercially available, for example, from Sigma-Aldrich, St. Louis, Mo. Further, the aryl sulfonium salts can be prepared by multiple methods.

Methods of preparation of triarylsulfonium salts have been described in the art. For example, methods using benzene as a starting material have been disclosed. The conventional method for producing triarylsulfonium chloride salts, as described in U.S. Pat. No. 2,807,648 and depicted in Scheme 1, comprises forming a mixture comprising arene (e.g. benzene) and aluminum chloride, and then reacting the mixture with sulfur monochloride followed by a reaction with chlorine gas to produce arylsulfonium chloride salts. Depending on the reaction conditions and stoichiometric ratio of the reactants, individual salts (structures I, II, or III in Scheme 1) or mixtures thereof can be prepared using this method.

Scheme 1

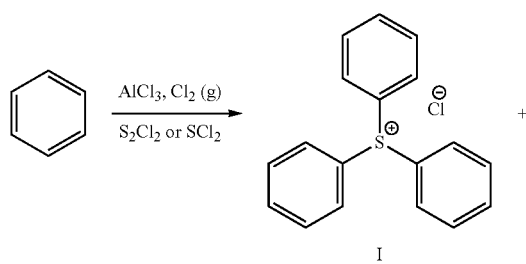

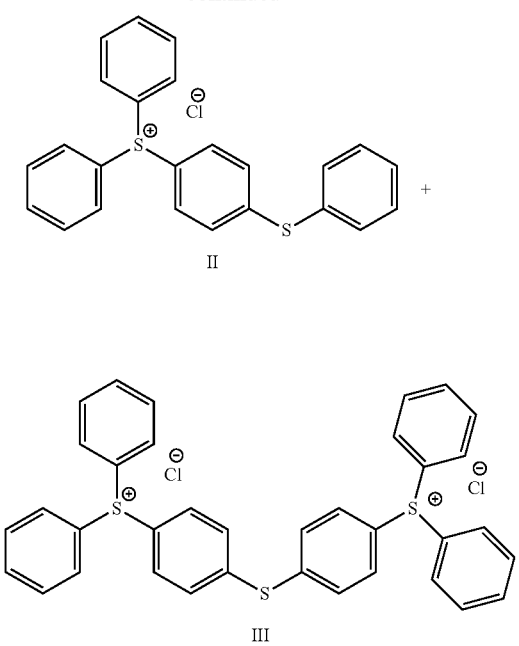

For example, diphenyl(4-(phenylthio)phenyl)sulfonium chloride (structure II in Scheme 1) can be prepared by the method described in Example 2 in U.S. Pat. No. 4,374,066, as shown in Scheme 2.

Scheme 2

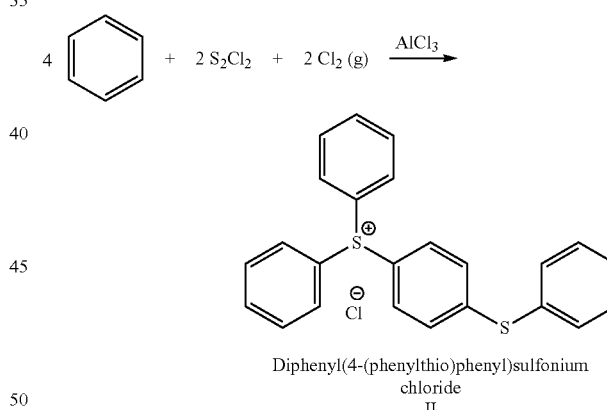

Diphenyl(4-(phenylthio)phenyl)sulfonium chloride
II

Bis-(diphenylsulfoniophenyl)-sulfide bis-chloride (structure III in Scheme 1) can also be prepared using this method, as described in detail in the comparative example of U.S. Pat. No. 4,400,541. This same method is also employed for synthesis of substituted arylsulfonium salts, as described in U.S. Patent Application No. 2005/0148679 A1.

Methods have also been taught for the synthesis of triarylsulfonium salts using diphenylsulfide as a starting material. Triarylsulfonium salts represented by structure II in Scheme 1 can be prepared through the reaction of diphenylsulfide and chlorine gas in the presence of a Friedel-Crafts catalyst (e.g. AlCl$_3$), as described in FR 2,475,078 and U.S. Pat. No. 4,374,066. The reaction proceeds as indicated in Scheme 3.

Scheme 3

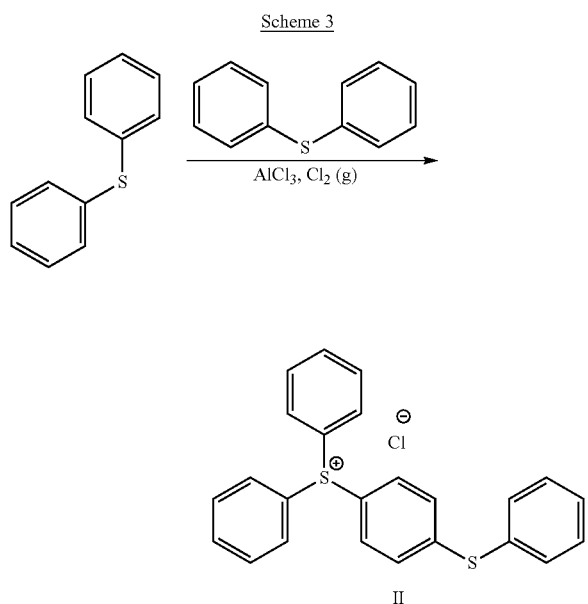

Methods for the synthesis of triarylsulfonium salts using diphenyldisulfide and benzene as starting materials have been described in the art. Triarylsulfonium salts represented by structure III in Scheme I can be prepared through the reaction of benzene, diphenyldisulfide (instead of diphenylsulfide), and chlorine gas in the presence of a Friedel-Crafts catalyst (e.g. AlCl₃), as described in U.S. Pat. No. 4,400,541 and depicted in Scheme 4.

Scheme 4

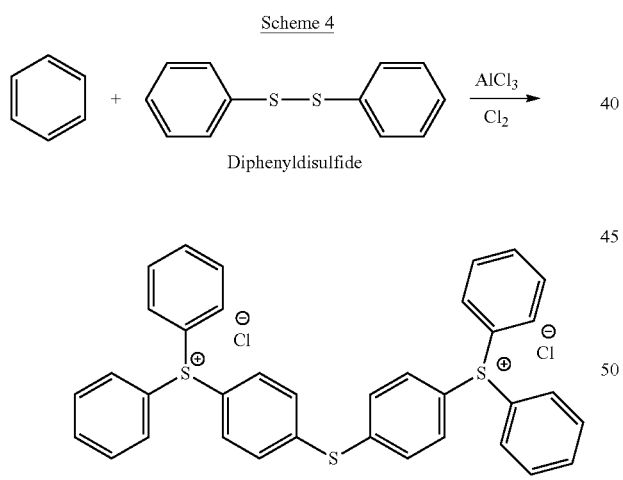

Diphenyldisulfide

Methods have also been described in the art for the synthesis of triarylsulfonium salts using diphenylsulfide and diphenylsulfoxide as starting materials. Aryl sulfonium salts represented by structures II and III in Scheme 5 can be produced via one-pot synthesis involving condensation of diarylsulfoxides with aromatic compounds in the presence of phosphorous pentaoxide/methane sulfonic acid (MSA), as described by Akhtar, Crivello, and Lee in "Synthesis of Aryl-Substituted Sulfonium Salts by the P₂O₅-Methanesulfonic Acid Promoted Condensation of Sulfoxides with Aromatic Compounds," J. Org. Chem. 1990, vol. 55, 4222-225.

Scheme 5

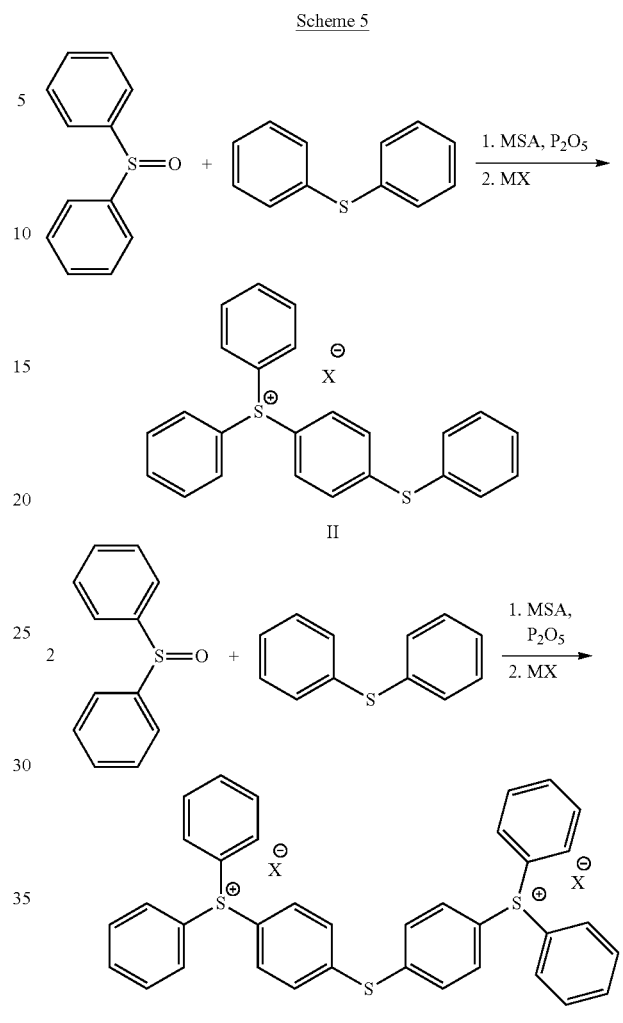

The effective amount of the aryl sulfonium salt is from about 1 to about 1000 ppm based on the total amount of injection fluid injected into the formation or production system, depending on the amount of bacteria and archaea that are present. Preferably, the effective amount of the aryl sulfonium salt is from about 1 to about 400 ppm based on the total amount of injection fluid injected into the formation or production system. More preferably, the effective amount of the aryl sulfonium salt is from about 10 to about 100 ppm based on the total amount of injection fluid injected into the formation or production system. Most preferably, the effective amount of the aryl sulfonium salt is from about 20 to about 75 ppm based on the total amount of water injected into the formation or production system.

The aryl sulfonium salts described herein significantly reduce microbial numbers, microbial activity, or a combination thereof and this effect can be quantified by the ATP standard disclosed in NACE TM0194-2014.

The hydrogen sulfide concentration in the hydrocarbon-containing system can be reduced by 25-100 percent, depending on the type and amount of sulfonium salt added and the absence or presence of a sand surface for the microbes to attach to and grow.

Additionally, the number of total active microorganisms or sulfur utilizing prokaryotes is reduced by 50-100 percent, depending on the type and amount of sulfonium salt added and the absence or presence of a sand surface for the microbes to attach to and grow.

The compositions can be applied to a gas or liquid produced or used in a waste-water process, a farm, a slaughter house, a land-fill, a sewage collection system, a municipality waste-water plant, a coking coal process, a paper mill, or a biofuel process.

In another aspect, disclosed is a method of controlling biofouling, the method comprising providing an effective amount of a composition of the invention into a system. The method can include controlling microorganism proliferation in a system used in the production, transportation, storage, and separation of crude oil and natural gas. The method can include controlling microbe proliferation in a system used in a coal-fired process, a waste-water process, a farm, a slaughter house, a land-fill, a sewage collection system, a municipality waste-water plant, a coking coal process, a paper mill process, or a biofuel process.

The composition can comprise an effective amount of the aryl sulfonium salt and a component selected from the group consisting of an organic solvent, a corrosion inhibitor, an asphaltene inhibitor, a paraffin inhibitor, a scale inhibitor, an emulsifier, a water clarifier, a dispersant, an emulsion breaker, a gas hydrate inhibitor, a biocide, a pH modifier, a surfactant, and a combination thereof.

The composition can comprise from about 20 to about 90 wt. % of an aryl sulfonium salt and from about 10 to about 80 wt. % of the component, preferably from about 50 to about 90 wt. % of one or more aryl sulfonium salts and from about 10 to about 50 wt. % of the component, and more preferably from about 65 to about 85 wt. % of one or more aryl sulfonium salts and from about 15 to about 35 wt. % of the component.

The component of the composition can comprise an organic solvent. The composition can comprise from about 1 to 80 wt. %, from about 5 to 50 wt. %, or from about 10 to 35 wt. % of the one or more organic solvents, based on total weight of the composition. The organic solvent can comprise an alcohol, a hydrocarbon, a ketone, an ether, an alkylene glycol, a glycol ether, an amide, a nitrile, a sulfoxide, an ester, or a combination thereof. Examples of suitable organic solvents include, but are not limited to, methanol, ethanol, propanol, isopropanol, butanol, 2-ethylhexanol, hexanol, octanol, decanol, 2-butoxyethanol, methylene glycol, ethylene glycol, 1,2-propylene glycol, 1,3-propylene glycol, diethyleneglycol monomethyl ether, diethylene glycol monoethyl ether, ethylene glycol monobutyl ether, ethylene glycol dibutyl ether, pentane, hexane, cyclohexane, methylcyclohexane, heptane, decane, dodecane, diesel, toluene, xylene, heavy aromatic naphtha, cyclohexanone, diisobutylketone, diethyl ether, propylene carbonate, N-methylpyrrolidinone, N,N-dimethylformamide, or a combination thereof.

The component of the composition can comprise a corrosion inhibitor. The composition can comprise from about 0.1 to 20 wt. %, 0.1 to 10 wt. %, or 0.1 to 5 wt. % of the corrosion inhibitors, based on total weight of the composition. A composition of the invention can comprise from 0.1 to 10 percent by weight of the corrosion inhibitors, based on total weight of the composition. The composition can comprise 1.0 wt %, 1.5 wt %, 2.0 wt %, 2.5 wt %, 3.0 wt %, 3.5 wt %, 4.0 wt %, 4.5 wt %, 5.0 wt %, 5.5 wt %, 6.0 wt %, 6.5 wt %, 7.0 wt %, 7.5 wt %, 8.0 wt %, 8.5 wt %, 9.0 wt %, 9.5 wt %, 10.0 wt %, 10.5 wt %, 11.0 wt %, 11.5 wt %, 12.0 wt %, 12.5 wt %, 13.0 wt %, 13.5 wt %, 14.0 wt %, 14.5 wt %, or 15.0 wt % by weight of the corrosion inhibitors, based on total weight of the composition. Each system can have its own requirements, and the weight percent of one or more additional corrosion inhibitors in the composition can vary with the system in which it is used.

The corrosion inhibitor can comprise an imidazoline compound, a quaternary ammonium compound, a pyridinium compound, or a combination thereof.

The corrosion inhibitor component can comprise an imidazoline. The imidazoline can be, for example, imidazoline derived from a diamine, such as ethylene diamine (EDA), diethylene triamine (DETA), triethylene tetraamine (TETA) etc. and a long chain fatty acid such as tall oil fatty acid (TOFA). The imidazoline can be an imidazoline of Formula (I) or an imidazoline derivative. Representative imidazoline derivatives include an imidazolinium compound of Formula (II) or a bis-quaternized compound of Formula (III).

The corrosion inhibitor component can include an imidazoline of Formula (I):

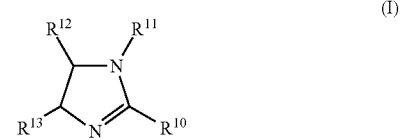

wherein $R^{10}$ is a $C_1$-$C_{20}$ alkyl or a $C_1$-$C_{20}$ alkoxyalkyl group; $R^{11}$ is hydrogen, $C_1$-$C_6$ alkyl, $C_1$-$C_6$ hydroxyalkyl, or $C_1$-$C_6$ arylalkyl; and $R^{12}$ and $R^{13}$ are independently hydrogen or a $C_1$-$C_6$ alkyl group. Preferably, the imidazoline includes an $R^{10}$ which is the alkyl mixture typical in tall oil fatty acid (TOFA), and $R^{11}$, $R^{12}$ and $R^{13}$ are each hydrogen.

The corrosion inhibitor component can include an imidazolinium compound of Formula (II):

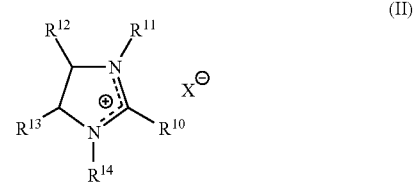

wherein $R^{10}$ is a $C_1$-$C_{20}$ alkyl or a $C_1$-$C_{20}$ alkoxyalkyl group; $R^{11}$ and $R^{14}$ are independently hydrogen, $C_1$-$C_6$ alkyl, $C_1$-$C_6$ hydroxyalkyl, or $C_1$-$C_6$ arylalkyl; $R^{12}$ and $R^{13}$ are independently hydrogen or a $C_1$-$C_6$ alkyl group; and $X^-$ is a halide (such as chloride, bromide, or iodide), carbonate, sulfonate, phosphate, or the anion of an organic carboxylic acid (such as acetate). Preferably, the imidazolinium compound includes 1-benzyl-1-(2-hydroxyethyl)-2-tall-oil-2-imidazolinium chloride.

The corrosion inhibitor can comprise a bis-quaternized compound having the formula (III):

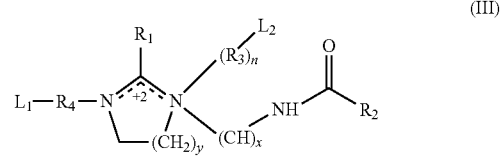

wherein $R_1$ and $R_2$ are each independently unsubstituted branched, chain or ring alkyl or alkenyl having from 1 to about 29 carbon atoms; partially or fully oxygenized, sulfurized, and/or phosphorylized branched, chain, or ring alkyl or alkenyl having from 1 to about 29 carbon atoms; or a combination thereof; $R_3$ and $R_4$ are each independently unsubstituted branched, chain or ring alkylene or alkenylene having from 1 to about 29 carbon atoms; partially or fully oxygenized, sulfurized, and/or phosphorylized branched, chain, or ring alkylene or alkenylene having from 1 to about 29 carbon atoms; or a combination thereof; $L_1$ and $L_2$ are each independently absent, H, —COOH, —SO$_3$H, —PO$_3$H$_2$, —COOR$_5$, —CONH$_2$, —CONHR$_5$, or —CON(R$_5$)$_2$; $R_5$ is each independently a branched or unbranched alkyl, aryl, alkylaryl, alkylheteroaryl, cycloalkyl, or heteroaryl group having from 1 to about 10 carbon atoms; n is 0 or 1, and when n is 0, $L_2$ is absent or H; x is from 1 to about 10; and y is from 1 to about 5. Preferably, $R_1$ and $R_2$ are each independently $C_6$-$C_{22}$ alkyl, $C_8$-$C_{20}$ alkyl, $C_{12}$-$C_{18}$ alkyl, $C_{16}$-$C_{18}$ alkyl, or a combination thereof; $R_3$ and $R_4$ are $C_1$-$C_{10}$ alkylene, $C_2$-$C_8$ alkylene, $C_2$-$C_6$ alkylene, or $C_2$-$C_3$ alkylene; n is 0 or 1; x is 2; y is 1; $R_3$ and $R_4$ are —C$_2$H$_2$—; $L_1$ is —COOH, —SO$_3$H, or —PO$_3$H$_2$; and $L_2$ is absent, H, —COOH, —SO$_3$H, or —PO$_3$H$_2$. For example, $R_1$ and $R_2$ can be derived from a mixture of tall oil fatty acids and are predominantly a mixture of $C_{17}H_{33}$ and $C_{17}H_{31}$ or can be $C_{16}$-$C_{18}$ alkyl; $R_3$ and $R_4$ can be $C_2$-$C_3$ alkylene such as —C$_2$H$_2$—; n is 1 and $L_2$ is —COOH or n is 0 and $L_2$ is absent or H; x is 2; y is 1; $R_3$ and $R_4$ are —C$_2$H$_2$—; and $L_1$ is —COOH.

It should be appreciated that the number of carbon atoms specified for each group of formula (III) refers to the main chain of carbon atoms and does not include carbon atoms that may be contributed by substituents.

The corrosion inhibitor can comprise a bis-quaternized imidazoline compound having the formula (III) wherein $R_1$ and $R_2$ are each independently $C_6$-$C_{22}$ alkyl, $C_8$-$C_{20}$ alkyl, $C_{12}$-$C_{18}$ alkyl, or $C_{16}$-$C_{18}$ alkyl or a combination thereof; $R_4$ is $C_1$-$C_{10}$ alkylene, $C_2$-$C_8$ alkylene, $C_2$-$C_6$ alkylene, or $C_2$-$C_3$ alkylene; x is 2; y is 1; n is 0; $L_1$ is —COOH, —SO$_3$H, or —PO$_3$H$_2$; and $L_2$ is absent or H. Preferably, a bis-quaternized compound has the formula (III) wherein $R_1$ and $R_2$ are each independently $C_{16}$-$C_{18}$ alkyl; $R_4$ is —C$_2$H$_2$—; x is 2; y is 1; n is 0; $L_1$ is —COOH, —SO$_3$H, or —PO$_3$H$_2$ and $L_2$ is absent or H.

The corrosion inhibitor can be a quaternary ammonium compound of Formula (IV):

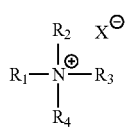

(IV)

wherein $R_1$, $R_2$, and $R_3$ are independently $C_1$ to $C_{20}$ alkyl, $R_4$ is methyl or benzyl, and X$^-$ is a halide or methosulfate.

Suitable alkyl, hydroxyalkyl, alkylaryl, arylalkyl or aryl amine quaternary salts include those alkylaryl, arylalkyl and aryl amine quaternary salts of the formula [N$^+$R$^{5a}$R$^{6a}$R$^{7a}$R$^{8a}$][X$^-$] wherein R$^{5a}$, R$^{6a}$, R$^{7a}$, and R$^{8a}$ contain one to 18 carbon atoms, and X is Cl, Br or I. For the quaternary salts, R$^{5a}$, R$^{6a}$, R$^{7a}$, and R$^{8a}$ can each be independently selected from the group consisting of alkyl (e.g., $C_1$-$C_{18}$ alkyl), hydroxyalkyl (e.g., $C_1$-$C_{18}$ hydroxyalkyl), and arylalkyl (e.g., benzyl). The mono or polycyclic aromatic amine salt with an alkyl or alkylaryl halide include salts of the formula [N$^+$R$^{5a}$R$^{6a}$R$^{7a}$R$^{8a}$][X$^-$] wherein R$^{5a}$, R$^{6a}$, R$^{7a}$, and R$^{8a}$ contain one to 18 carbon atoms and at least one aryl group, and X is Cl, Br or I.

Suitable quaternary ammonium salts include, but are not limited to, a tetramethyl ammonium salt, a tetraethyl ammonium salt, a tetrapropyl ammonium salt, a tetrabutyl ammonium salt, a tetrahexyl ammonium salt, a tetraoctyl ammonium salt, a benzyltrimethyl ammonium salt, a benzyltriethyl ammonium salt, a phenyltrimethyl ammonium salt, a phenyltriethyl ammonium salt, a cetyl benzyldimethyl ammonium salt, a hexadecyl trimethyl ammonium salt, a dimethyl alkyl benzyl quaternary ammonium salt, a monomethyl dialkyl benzyl quaternary ammonium salt, or a trialkyl benzyl quaternary ammonium salt, wherein the alkyl group has about 6 to about 24 carbon atoms, about 10 and about 18 carbon atoms, or about 12 to about 16 carbon atoms. The quaternary ammonium salt can be a benzyl trialkyl quaternary ammonium salt, a benzyl triethanolamine quaternary ammonium salt, or a benzyl dimethylaminoethanolamine quaternary ammonium salt.

The corrosion inhibitor component can comprise a pyridinium salt such as those represented by Formula (V):

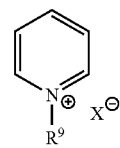

(V)

wherein $R^9$ is an alkyl group, an aryl group, or an arylalkyl group, wherein said alkyl groups have from 1 to about 18 carbon atoms and X$^-$ is a halide such as chloride, bromide, or iodide. Among these compounds are alkyl pyridinium salts and alkyl pyridinium benzyl quats. Exemplary compounds include methyl pyridinium chloride, ethyl pyridinium chloride, propyl pyridinium chloride, butyl pyridinium chloride, octyl pyridinium chloride, decyl pyridinium chloride, lauryl pyridinium chloride, cetyl pyridinium chloride, benzyl pyridinium chloride and an alkyl benzyl pyridinium chloride, preferably wherein the alkyl is a $C_1$-$C_6$ hydrocarbyl group. Preferably, the pyridinium compound includes benzyl pyridinium chloride.

The corrosion inhibitor components can include additional corrosion inhibitors such as phosphate esters, monomeric or oligomeric fatty acids, or alkoxylated amines.

The corrosion inhibitor component can comprise a phosphate ester. Suitable mono-, di- and tri-alkyl as well as alkylaryl phosphate esters and phosphate esters of mono, di, and triethanolamine typically contain between from 1 to about 18 carbon atoms. Preferred mono-, di- and trialkyl phosphate esters, alkylaryl or arylalkyl phosphate esters are those prepared by reacting a $C_3$-$C_{18}$ aliphatic alcohol with phosphorous pentoxide. The phosphate intermediate interchanges its ester groups with triethylphosphate producing a more broad distribution of alkyl phosphate esters.

Alternatively, the phosphate ester can be made by admixing with an alkyl diester, a mixture of low molecular weight alkyl alcohols or diols. The low molecular weight alkyl alcohols or diols preferably include $C_6$ to $C_{10}$ alcohols or diols. Further, phosphate esters of polyols and their salts containing one or more 2-hydroxyethyl groups, and hydroxylamine phosphate esters obtained by reacting polyphosphoric acid or phosphorus pentoxide with hydroxylamines such as diethanolamine or triethanolamine are preferred.

The corrosion inhibitor component can include a monomeric or oligomeric fatty acid. Preferred monomeric or oligomeric fatty acids are $C_{14}$-$C_{22}$ saturated and unsaturated fatty acids as well as dimer, trimer and oligomer products obtained by polymerizing one or more of such fatty acids.

The corrosion inhibitor component can comprise an alkoxylated amine. The alkoxylated amine can be an ethoxylated alkyl amine. The alkoxylated amine can be ethoxylated tallow amine.

The component of the composition can comprise an organic sulfur compound, such as a mercaptoalkyl alcohol, mercaptoacetic acid, thioglycolic acid, 3,3'-dithiodipropionic acid, sodium thiosulfate, thiourea, L-cysteine, tert-butyl mercaptan, sodium thiosulfate, ammonium thiosulfate, sodium thiocyanate, ammonium thiocyanate, sodium metabisulfite, or a combination thereof. Preferably, the mercaptoalkyl alcohol comprises 2-mercaptoethanol. The organic sulfur compound can constitute 0.5 to 15 wt. % of the composition, based on total weight of the composition, preferably about 1 to about 10 wt. % and more preferably about 1 to about 5 wt. %. The organic sulfur compound can constitute 1, 2, 3, 4, 5, 6, 7, 8, 9, 10, 11, 12, 13, 14 or 15 wt. % of the composition.

The composition can be substantially free of or free of any organic sulfur compound other than the compound of formula (1). A composition is substantially free of any organic sulfur compound if it contains an amount of organic sulfur compound below the amount that will produce hydrogen sulfide gas upon storage at a temperature of 25° C. and ambient pressure.

The component of the composition can further include a demulsifier. Preferably, the demulsifier comprises an oxyalkylate polymer, such as a polyalkylene glycol. The demulsifier can constitute from about 0.1 to 10 wt. %, from about 0.5 to 5 wt. %, or from about 0.5 to 4 wt. % of the composition, based on total weight of the composition. The demulsifier can constitute 0.5, 1, 1.5, 2, 2.5, 3, 3.5, 4, 4.5 or 5 wt. % of the composition.

The component of the composition can include an asphaltene inhibitor. The composition can comprise from about 0.1 to 10 wt. %, from about 0.1 to 5 wt. %, or from about 0.5 to 4 wt. % of an asphaltene inhibitor, based on total weight of the composition. Suitable asphaltene inhibitors include, but are not limited to, aliphatic sulfonic acids; alkyl aryl sulfonic acids; aryl sulfonates; lignosulfonates; alkylphenol/aldehyde resins and similar sulfonated resins; polyolefin esters; polyolefin imides; polyolefin esters with alkyl, alkylenephenyl or alkylenepyridyl functional groups; polyolefin amides; polyolefin amides with alkyl, alkylenephenyl or alkylenepyridyl functional groups; polyolefin imides with alkyl, alkylenephenyl or alkylenepyridyl functional groups; alkenyl/vinyl pyrrolidone copolymers; graft polymers of polyolefins with maleic anhydride or vinyl imidazole; hyperbranched polyester amides; polyalkoxylated asphaltenes, amphoteric fatty acids, salts of alkyl succinates, sorbitan monooleate, and polyisobutylene succinic anhydride.

The component of the composition can include an additional paraffin inhibitor. The composition can comprise from about 0.1 to 10 wt. %, from about 0.1 to 5 wt. %, or from about 0.5 to 4 wt. % of an additional paraffin inhibitor, based on total weight of the composition. Suitable additional paraffin inhibitors include, but are not limited to, paraffin crystal modifiers, and dispersant/crystal modifier combinations. Suitable paraffin crystal modifiers include, but are not limited to, alkyl acrylate copolymers, alkyl acrylate vinylpyridine copolymers, ethylene vinyl acetate copolymers, maleic anhydride ester copolymers, branched polyethylenes, naphthalene, anthracene, microcrystalline wax and/or asphaltenes. Suitable paraffin dispersants include, but are not limited to, dodecyl benzene sulfonate, oxyalkylated alkylphenols, and oxyalkylated alkylphenolic resins.

The component of the composition can include a scale inhibitor. The composition can comprise from about 0.1 to 20 wt. %, from about 0.5 to 10 wt. %, or from about 1 to 10 wt. % of a scale inhibitor, based on total weight of the composition. Suitable scale inhibitors include, but are not limited to, phosphates, phosphate esters, phosphoric acids, phosphonates, phosphonic acids, polyacrylamides, salts of acrylamidomethyl propane sulfonate/acrylic acid copolymer (AMPS/AA), phosphinated maleic copolymer (PHOS/MA), and salts of a polymaleic acid/acrylic acid/acrylamidomethyl propane sulfonate terpolymer (PMA/AA/AMPS).

The component of the composition can include an emulsifier. The composition can comprise from about 0.1 to 10 wt. %, from about 0.5 to 5 wt. %, or from about 0.5 to 4 wt. % of an emulsifier, based on total weight of the composition. Suitable emulsifiers include, but are not limited to, salts of carboxylic acids, products of acylation reactions between carboxylic acids or carboxylic anhydrides and amines, and alkyl, acyl and amide derivatives of saccharides (alkylsaccharide emulsifiers).

The component of the composition can include a water clarifier. The composition can comprise from about 0.1 to 10 wt. %, from about 0.5 to 5 wt. %, or from about 0.5 to 4 wt. % of a water clarifier, based on total weight of the composition. Suitable water clarifiers include, but are not limited to, inorganic metal salts such as alum, aluminum chloride, and aluminum chlorohydrate, or organic polymers such as acrylic acid based polymers, acrylamide based polymers, polymerized amines, alkanolamines, thiocarbamates, and cationic polymers such as diallyldimethylammonium chloride (DADMAC).

The component of the composition can include a dispersant. The composition can comprise from about 0.1 to 10 wt. %, from about 0.5 to 5 wt. %, or from about 0.5 to 4 wt. % of a dispersant, based on total weight of the composition. Suitable dispersants include, but are not limited to, aliphatic phosphonic acids with 2-50 carbons, such as hydroxyethyl diphosphonic acid, and aminoalkyl phosphonic acids, e.g. polyaminomethylene phosphonates with 2-10 N atoms e.g. each bearing at least one methylene phosphonic acid group; examples of the latter are ethylenediamine tetra(methylene phosphonate), diethylenetriamine penta(methylene phosphonate), and the triamine- and tetramine-polymethylene phosphonates with 2-4 methylene groups between each N atom, at least 2 of the numbers of methylene groups in each phosphonate being different. Other suitable dispersion agents include lignin, or derivatives of lignin such as lignosulfonate and naphthalene sulfonic acid and derivatives.

The component of the composition can include an emulsion breaker. The composition can comprise from about 0.1 to 10 wt. %, from about 0.5 to 5 wt. %, or from about 0.5 to 4 wt. % of an emulsion breaker, based on total weight of the composition. Suitable emulsion breakers include, but are not limited to, dodecylbenzylsulfonic acid (DDBSA), the sodium salt of xylenesulfonic acid (NAXSA), epoxylated and propoxylated compounds, anionic, cationic and nonionic surfactants, and resins, such as phenolic and epoxide resins.

The component of the composition can include a hydrogen sulfide scavenger. The composition can comprise from about 1 to 50 wt. %, from about 1 to 40 wt. %, or from about 1 to 30 wt. % of a hydrogen sulfide scavenger, based on total weight of the composition. Suitable additional hydrogen sulfide scavengers include, but are not limited to, oxidants (e.g., inorganic peroxides such as sodium peroxide or chlorine dioxide); aldehydes (e.g., of 1-10 carbons such as formaldehyde, glyoxal, glutaraldehyde, acrolein, or methacrolein; triazines (e.g., monoethanolamine triazine, monomethylamine triazine, and triazines from multiple amines or mixtures thereof); condensation products of secondary or tertiary amines and aldehydes, and condensation products of alkyl alcohols and aldehydes.

The component of the composition can include a gas hydrate inhibitor. The composition can comprise from about 0.1 to 25 wt. %, from about 0.1 to 20 wt. %, or from about 0.3 to 20 wt. % of a gas hydrate inhibitor, based on total weight of the composition. Suitable gas hydrate inhibitors include, but are not limited to, thermodynamic hydrate inhibitors (THI), kinetic hydrate inhibitors (KHI), and anti-agglomerates (AA). Suitable thermodynamic hydrate inhibitors include, but are not limited to, sodium chloride, potassium chloride, calcium chloride, magnesium chloride, sodium bromide, formate brines (e.g. potassium formate), polyols (such as glucose, sucrose, fructose, maltose, lactose, gluconate, monoethylene glycol, diethylene glycol, triethylene glycol, mono-propylene glycol, dipropylene glycol, tripropylene glycols, tetrapropylene glycol, monobutylene glycol, dibutylene glycol, tributylene glycol, glycerol, diglycerol, triglycerol, and sugar alcohols (e.g. sorbitol, mannitol)), methanol, propanol, ethanol, glycol ethers (such as diethyleneglycol monomethylether, ethyleneglycol monobutylether), and alkyl or cyclic esters of alcohols (such as ethyl lactate, butyl lactate, methylethyl benzoate).

The component of the composition can include a kinetic hydrate inhibitor. The composition can comprise from about 5 to 30 wt. %, from about 5 to 25 wt. %, or from about 10 to 25 wt. % of a kinetic hydrate inhibitor, based on total weight of the composition. Suitable kinetic hydrate inhibitors and anti-agglomerates include, but are not limited to, polymers and copolymers, polysaccharides (such as hydroxyethylcellulose (HEC), carboxymethylcellulose (CMC), starch, starch derivatives, and xanthan), lactams (such as polyvinylcaprolactam, polyvinyl lactam), pyrrolidones (such as polyvinyl pyrrolidone of various molecular weights), surfactants (such as fatty acid salts, ethoxylated alcohols, propoxylated alcohols, sorbitan esters, ethoxylated sorbitan esters, polyglycerol esters of fatty acids, alkyl glucosides, alkyl polyglucosides, alkyl sulfates, alkyl sulfonates, alkyl ester sulfonates, alkyl aromatic sulfonates, alkyl betaine, alkyl amido betaines), hydrocarbon based dispersants (such as lignosulfonates, iminodisuccinates, polyaspartates), amino acids, and proteins.

The component of the composition can include a biocide. The composition can comprise from about 0.1 to 10 wt. %, from about 0.5 to 5 wt. %, or from about 0.5 to 4 wt. % of a biocide, based on total weight of the composition. Suitable biocides include, but are not limited to, oxidizing and non-oxidizing biocides. Suitable non-oxidizing biocides include, for example, aldehydes (e.g., formaldehyde, glutaraldehyde, and acrolein), amine-type compounds (e.g., quaternary amine compounds and cocodiamine), halogenated compounds (e.g., 2-bromo-2-nitropropane-3-diol (Bronopol) and 2-2-dibromo-3-nitrilopropionamide (DB-NPA)), sulfur compounds (e.g., isothiazolone, carbamates, and metronidazole), and quaternary phosphonium salts (e.g., tetrakis(hydroxymethyl)-phosphonium sulfate (THPS)). Suitable oxidizing biocides include, for example, sodium hypochlorite, trichloroisocyanuric acids, dichloroisocyanuric acid, calcium hypochlorite, lithium hypochlorite, chlorinated hydantoins, stabilized sodium hypobromite, activated sodium bromide, brominated hydantoins, chlorine dioxide, ozone, and peroxides.

The component of the composition can include a pH modifier. The composition can comprise from about 0.1 to 20 wt. %, from about 0.5 to 10 wt. %, or from about 0.5 to 5 wt. % of a pH modifier, based on total weight of the composition. Suitable pH modifiers include, but are not limited to, alkali hydroxides, alkali carbonates, alkali bicarbonates, alkaline earth metal hydroxides, alkaline earth metal carbonates, alkaline earth metal bicarbonates and mixtures or combinations thereof. Exemplary pH modifiers include sodium hydroxide, potassium hydroxide, calcium hydroxide, calcium oxide, sodium carbonate, potassium carbonate, sodium bicarbonate, potassium bicarbonate, magnesium oxide, and magnesium hydroxide.

The component of the composition can include a surfactant. The composition can comprise from about 0.1 to 10 wt. %, from about 0.5 to 5 wt. %, or from about 0.5 to 4 wt. % of a surfactant, based on total weight of the composition. Suitable surfactants include, but are not limited to, anionic surfactants and nonionic surfactants. Anionic surfactants include alkyl aryl sulfonates, olefin sulfonates, paraffin sulfonates, alcohol sulfates, alcohol ether sulfates, alkyl carboxylates and alkyl ether carboxylates, and alkyl and ethoxylated alkyl phosphate esters, and mono and dialkyl sulfosuccinates and sulfosuccinamates. Nonionic surfactants include alcohol alkoxylates, alkylphenol alkoxylates, block copolymers of ethylene, propylene and butylene oxides, alkyl dimethyl amine oxides, alkyl-bis(2-hydroxyethyl) amine oxides, alkyl amidopropyl dimethyl amine oxides, alkylamidopropyl-bis(2-hydroxyethyl) amine oxides, alkyl polyglucosides, polyalkoxylated glycerides, sorbitan esters and polyalkoxylated sorbitan esters, and alkoyl polyethylene glycol esters and diesters. Also included are betaines and sultanes, amphoteric surfactants such as alkyl amphoacetates and amphodiacetates, alkyl amphopropionates and amphodipropionates, and alkyliminodipropionate.

Paraffin inhibitor compositions made according to the invention can further include additional functional agents or additives that provide a beneficial property. For example, additional agents or additives can be sequestrants, solubilizers, lubricants, buffers, cleaning agents, rinse aids, preservatives, binders, thickeners or other viscosity modifiers, processing aids, carriers, water-conditioning agents, foam inhibitors or foam generators, threshold agents or systems, aesthetic enhancing agents (i.e., dyes, odorants, perfumes), or other additives suitable for formulation with a corrosion inhibitor composition, and mixtures thereof. Additional agents or additives will vary according to the particular corrosion inhibitor composition being manufactured and its intend use as one skilled in the art will appreciate.

Alternatively, the compositions can not contain any of the additional agents or additives.

Additionally, the aryl sulfonium salt can be formulated into a treatment fluid comprising the following components. These formulations include the ranges of the components listed and can optionally include additional agents.

| Component | 1 | 2 | 3 | 4 | 5 | 6 | 7 | 8 | 9 | 10 | 11 | 12 |
|---|---|---|---|---|---|---|---|---|---|---|---|---|
| Aryl sulfonium salt | 30-90 | 30-90 | 30-90 | 30-90 | 30-90 | 30-90 | 65-85 | 65-85 | 65-85 | 65-85 | 65-85 | 30-90 |
| Organic solvent | 10-35 | | | | | | 10-35 | | | | | 10-35 |
| Corrosion inhibitor | 0.1-20 | 0.1-20 | | | | | 0.1-20 | 0.1-20 | | | | 0.1-20 |
| Asphaltene inhibior | 0.1-5 | 0.1-5 | 0.1-5 | 0.1-5 | | | 0.1-5 | 0.1-5 | 0.1-5 | | | 0.1-5 |
| Paraffin inhibitor | | | | | | | | | | | | |
| Scale inhibitor | 1-10 | 1-10 | 1-10 | 1-10 | 1-10 | | 1-10 | 1-10 | 1-10 | 1-10 | | 1-10 |
| Emulsifier | | | | | | | | | | | | |
| Water clarifier | | | | | | | | | | | | |
| Dispersant | | | | | | | | | | | | |
| Emulsion breaker | | | | | | | | | | | | |
| Gas hydrate inhibitor | | | | | | | | | | | | 0.1-25 |
| Biocide | 0.5-5 | 0.5-5 | 0.5-5 | 0.5-5 | 0.5-5 | 0.5-5 | 0.5-5 | 0.5-5 | 0.5-5 | 0.5-5 | 0.5-5 | |
| pH modifier | | | | | | | | | | | | |
| Surfactant | | | | | | | | | | | | |

| Component | 13 | 14 | 15 | 16 | 17 | 18 | 19 | 20 | 21 | 22 | 23 | 24 |
|---|---|---|---|---|---|---|---|---|---|---|---|---|
| Aryl sulfonium salt | 30-90 | 30-90 | 30-90 | 30-90 | 30-90 | 30-90 | 65-85 | 65-85 | 65-85 | 65-85 | 65-85 | 65-85 |
| Organic solvent | | | | | | | | | | | | |
| Corrosion inhibitor | 0.1-20 | 0.1-20 | 0.1-20 | 0.1-20 | 0.1-20 | 0.1-20 | 0.1-20 | 0.1-20 | 0.1-20 | 0.1-20 | 0.1-20 | 0.1-20 |
| Asphaltene inhibior | 0.1-5 | | | | | | 0.1-5 | | | | | |
| Paraffin inhibitor | | | | | | | | | | | | |
| Scale inhibitor | 1-10 | 1-10 | | | 1-10 | | 1-10 | 1-10 | | | | 1-10 |
| Emulsifier | | | | | | | | | | | | |
| Water clarifier | | | | | | | | | | | | |
| Dispersant | | | | | | | | | | | | |
| Emulsion breaker | | | | | | | | | | | | |
| Gas hydrate inhibitor | 0.1-25 | 0.1-25 | 0.1-25 | | | | 0.1-25 | 0.1-25 | 0.1-25 | | 0.1-25 | |
| Biocide | | | | | | 0.5-5 | 0.5-5 | 0.5-5 | 0.5-5 | 0.5-5 | | |
| pH modifier | | | | | | | | | | | | |
| Surfactant | | | | | | | | | | | | |

Unless otherwise indicated, an alkyl group as described herein alone or as part of another group is an optionally substituted linear saturated monovalent hydrocarbon substituent containing from one to sixty carbon atoms and preferably one to thirty carbon atoms in the main chain or eight to thirty carbon atoms in the main chain, or an optionally substituted branched saturated monovalent hydrocarbon substituent containing three to sixty carbon atoms, and preferably eight to thirty carbon atoms in the main chain. Examples of unsubstituted alkyl groups include methyl, ethyl, n-propyl, i-propyl, n-butyl, i-butyl, s-butyl, t-butyl, n-pentyl, i-pentyl, s-pentyl, t-pentyl, and the like.

The term alkoxy as used herein or alone or as part of another group is an —OR group, wherein the R group is a substitued or unsubstituted alkyl group as defined herein.

The terms "aryl" or "ar" as used herein alone or as part of another group (e.g., aralkyl) denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl. The term "aryl" also includes heteroaryl.

The term "substituted" as in "substituted aryl," "substituted alkyl," and the like, means that in the group in question (i.e., the alkyl, aryl or other group that follows the term), at least one hydrogen atom bound to a carbon atom is replaced with one or more substituent groups such as hydroxy (—OH), alkylthio, phosphino, amido (—CON($R_A$)($R_B$), wherein $R_A$ and $R_B$ are independently hydrogen, alkyl, or aryl), amino(—N($R_A$)($R_B$), wherein $R_A$ and $R_B$ are independently hydrogen, alkyl, or aryl), halo (fluoro, chloro, bromo, or iodo), silyl, nitro (—$NO_2$), an ether (—$OR_A$ wherein $R_A$ is alkyl or aryl), an ester (—OC(O)$R_A$ wherein $R_A$ is alkyl or aryl), keto (—C(O)$R_A$ wherein $R_A$ is alkyl or aryl), heterocyclo, and the like. When the term "substituted" introduces a list of possible substituted groups, it is intended that the term apply to every member of that group. That is, the phrase "optionally substituted alkyl or aryl" is to be interpreted as "optionally substituted alkyl or optionally substituted aryl."

The term "heterocyclo," "heterocycle," or "heterocyclyl," as used herein, refers to a monocyclic, bicyclic, or tricyclic group containing 1 to 4 heteroatoms selected from N, O, S(O)$_n$, P(O)$_n$, P$R^z$, NH or N$R^z$, wherein $R^z$ is a suitable substituent. Heterocyclic groups optionally contain one or two double bonds. Heterocyclic groups include, but are not limited to, azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydro-thiadiazinyl, morpholinyl, oxetanyl, tetrahydrodiazinyl, oxazinyl, oxathiazinyl, indolinyl, isoindolinyl, quinuclidinyl, chromanyl, isochromanyl, and benzoxazinyl. Examples of monocyclic saturated or partially saturated ring systems are tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperazin-1-yl, piperazin-2-yl, piperazin-3-yl, 1,3-oxazolidin-3-yl, isothiazolidine, 1,3-thiazolidin-3-yl, 1,2-pyrazolidin-2-yl, 1,3-pyrazolidin-1-yl, thiomorpholin-yl, 1,2-tetrahydrothiazin-2-yl, 1,3-tetrahydrothiazin-3-yl, tetrahydrothiadiazin-yl, morpholin-yl, 1,2-tetrahydrodiazin-2-yl, 1,3-tetrahydrodiazin-1-yl, 1,4-oxazin-2-yl, and 1,2,5-oxathiazin-4-yl. Heterocyclic groups can be unsubstituted or substituted by one or more suitable substituents, preferably 1 to 3 suitable substituents, as defined above.

Having described the invention in detail, it will be apparent that modifications and variations are possible without departing from the scope of the invention defined in the appended claims.

EXAMPLES

The following non-limiting examples are provided to further illustrate the present invention.

Example 1

Synthesis of 4,4'-bis-(diphenyl sulfonio phenyl) sulfide bis-chloride

To proceed with synthesis of 4,4'-bis-(diphenyl sulfonio phenyl) sulfide bis-chloride, benzene (230 g) and anhydrous aluminum chloride (80 g) are added into a jacketed reactor equipped with mechanical mixer, chlorine gas inlet, gas vent (with scrubber) and temperature probe. The mixture is stirred to obtain clear solution and cooled to about 10° C. Sulfur monochloride (50 g) is added next, keeping the reaction temperature at 10°-18° C. The reaction mixture is stirred for one hour at 10°-18° C. Next dry chlorine (100 g) is sparged into reactor. After completion the reaction mixture is poured onto ice (300 g) and stirred until the aluminum chloride is completely dissolved. The solution is heated to 60° C. and is allowed to stand. The product layer is drained. The product layer is extracted with an aqueous sulfuric acid solution (25 g of $H_2SO_4$ in 300 g water), the mixture is settled and the lower product layer is separated. The product layer is extracted next with an aqueous solution of sodium hydroxide (20 g of 50% NaOH in 96 ml water). Aqueous solution of the product is used as is.

Example 2

Synthesis of diphenyl(4-(phenylthio)phenyl)sulfonium chloride

To proceed with synthesis of diphenyl(4-(phenylthio)phenyl) sulfonium chloride, diphenylsulfide (37.2 g) and anhydrous aluminum chloride (13.3 g) are added into a jacketed reactor equipped with mechanical mixer, chlorine gas inlet, gas vent (with scrubber) and temperature probe. The mixture is stirred to obtain clear solution and cooled to about 10° C. Next dry chlorine (10 g) is sparged into reactor keeping the reaction temperature at 10-18° C. After completion the reaction mixture is poured onto ice (100 g) and stirred until the aluminum chloride is completely dissolved. The solution is heated to 40° C. and is allowed to stand. The product layer is drained. The product layer is extracted with an aqueous sulfuric acid solution (5 g of $H_2SO_4$ in 100 g water), the mixture is settled and the lower product layer is separated. The product layer is extracted next with an aqueous solution of sodium hydroxide (5 g of 50% NaOH in 50 ml water). Aqueous solution of the product is used as is.

Example 3

Sulfide Inhibition

A sulfide test kit (Code 4456-01, available from LaMotte) was used to test the efficacy of a sulfonium salt mixture composed of triphenyl sulfonium chloride, diphenyl (4-phenylthio)phenylsulfonium chloride, and (thiodi-4,1-phenylene)bis-diphenylsulfonium dichloride in concentrations of 10 ppm, 50 ppm, and 100 ppm, the results of which are shown in Table 1. The results demonstrate that an increased concentration of the sulfonium salt correspondingly decreases the sulfide concentration.

TABLE 1

| Treatment | Average sulfide concentration (ppm) |
|---|---|
| Untreated | 20 |
| Sulfonium salt mixture (10 ppm) | 11.2 |
| Sulfonium salt mixture (50 ppm) | 1.8 |
| Sulfonium salt mixture (100 ppm) | 0.25 |

Example 4

Reduction in Active Microbes and Sulfide Inhibition with or without a Sand Surface An ATP test kit (Code QGA-100C, available from LumiNultra) was used to test the ability of a sulfonium salt mixture composed of triphenyl sulfonium chloride, diphenyl (4-phenylthio)phenylsulfonium chloride, and (thiodi-4,1-phenylene)bis-diphenylsulfonium dichloride in concentrations of 10 ppm, 50 ppm, and 100 ppm to reduce the number of active microbes from an oilfield produced water sample in the presence of a sand growth matrix (Product number 274739, available from Sigma-Aldrich). A sulfide test kit (Code 4456-01, available from LaMotte) was also used to monitor the sulfide levels during the test. The results of both tests are shown in Table 2. The results demonstrate that an increased concentration of the sulfonium salt correspondingly decreases the number of active microbes and the sulfide concentration, regardless of the presence or absence of a sand surface.

TABLE 2

| Test Condition | Average reduction in active microbes | Average reduction in sulfide |
|---|---|---|
| Sulfonium salt mixture (10 ppm) | ND | 25.0% |
| Sulfonium salt mixture (50 ppm) | 91.2% | 98.3% |
| Sulfonium salt mixture (100 ppm) | 94.4% | 100.0% |
| Sulfonium salt mixture (10 ppm) + sand surface | ND | 45.4% |
| Sulfonium salt mixture (50 ppm) + sand surface | 54.5% | 82.5% |
| Sulfonium salt mixture (100 ppm) + sand surface | 92.4% | 99.7% |

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above methods without departing from the scope of the invention, it is intended that all matter contained in the above description shall be interpreted as illustrative and not in a limiting sense.

The invention claimed is:

1. A method for reducing a concentration of hydrogen sulfide in a hydrocarbon-containing system comprising a water injection system, a hydrocarbon extraction system, or a hydrocarbon production system comprising administering an effective amount of an aryl sulfonium salt into the water injection system, the hydrocarbon extraction system, or the hydrocarbon production system, wherein the aryl sulfonium salt inhibits the production of hydrogen sulfide by a sulfur utilizing prokaryote, wherein the aryl sulfonium salt comprises (i) a cation of Formula 1 and a cation of Formula 2, (ii) a cation of Formula 1 and a dication of Formula 3, (iii) a cation of Formula 2 and a dication of Formula 3, or (iv) a cation of Formula 1, a cation of Formula 2, and a dication of Formula 3, wherein the cation of Formula 1, the cation of Formula 2, and the dication of Formula 3 have the following structures:

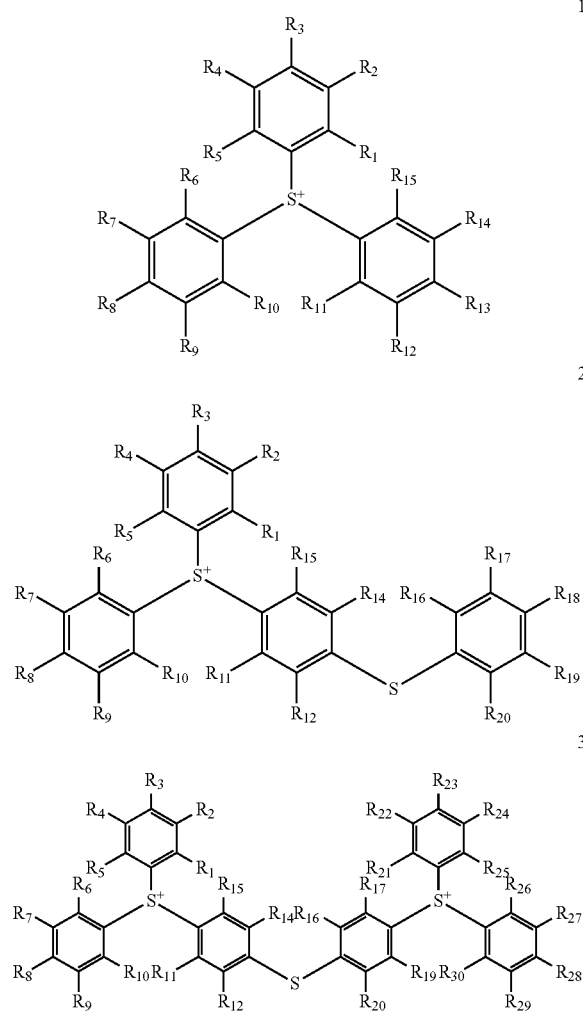

2. The method of claim 1, wherein the aryl sulfonium salt comprises the cation of Formula 1 and the dication of Formula 3.

3. The method of claim 1, wherein the aryl sulfonium salt comprises the cation of Formula 2 and the dication of Formula 3.

4. The method of claim 1, wherein the aryl sulfonium salt comprises the cation of Formula 1, the cation of Formula 2, and the dication of Formula 3.

5. The method of claim 4, wherein one to six of $R_1$-$R_{30}$ are each independently an alkyl group and the balance are hydrogen.

6. The method of claim 4, wherein one to three of $R_1$-$R_{30}$ are each independently an alkyl group and the balance are hydrogen.

7. The method of claim 4, wherein $R_1$-$R_{30}$ are hydrogen.

8. The method of claim 1, wherein the hydrocarbon-containing system comprises the hydrocarbon extraction system or the hydrocarbon production system and the effective amount of the aryl sulfonium salt is administered by injecting an injection fluid containing the aryl sulfonium salt into the hydrocarbon extraction system or the hydrocarbon production system.

9. The method of claim 8, wherein the hydrocarbon extraction system or the hydrocarbon production system is a subterranean hydrocarbon-containing formation, a well, a pipeline, a fluid separation vessel, a floating production storage vessel, an offloading vessel, a refinery, or a storage system.

10. The method of claim 1, wherein the aryl sulfonium salt comprises triaryl sulfonium chloride, diphenyl (4-phenylthio)phenylsulfonium chloride, and (thiodi-4,1-phenylene)bis-diphenylsulfonium dichloride.

11. The method of claim 1, wherein the effective amount of the aryl sulfonium salt is administered by injecting an injection fluid containing from about 1 to about 1000 ppm by weight of the aryl sulfonium salt based on the total amount of injection fluid injected into the hydrocarbon-containing system.

12. The method of claim 1, wherein the aryl sulfonium salt is administered by injecting a solution containing the effective amount of the aryl sulfonium salt into the water injection system, the hydrocarbon extraction system, or the hydrocarbon production system intermittently.

13. The method of claim 1, wherein the aryl sulfonium salt comprises the cation of Formula 1 and the cation of Formula 2.

* * * * *

UNITED STATES PATENT AND TRADEMARK OFFICE
CERTIFICATE OF CORRECTION

PATENT NO. : 10,301,553 B2
APPLICATION NO. : 15/445707
DATED : May 28, 2019
INVENTOR(S) : Brett Geissler et al.

Page 1 of 1

It is certified that error appears in the above-identified patent and that said Letters Patent is hereby corrected as shown below:

In the Claims

On Column 21, Line 50:
Below the third structure of Claim 1, insert:
--wherein R1-R30 are independently hydrogen, an alkyl group, an alkoxy group, an aryl group, or a heterocyclo group.--

Signed and Sealed this
Eighth Day of December, 2020

Andrei Iancu
*Director of the United States Patent and Trademark Office*